United States Patent
Messenger et al.

(10) Patent No.: US 6,306,660 B1
(45) Date of Patent: Oct. 23, 2001

(54) METHOD FOR IMPROVING THE ACCURACY OF THE SEMI-QUANTITATIVE DETERMINATION OF ANALYTE IN FLUID SAMPLES

(75) Inventors: Koleen K. Messenger; Michael J. Pugia, both of Granger; Jane F. Wallace, South Bend, all of IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/484,293

(22) Filed: Jan. 18, 2000

Related U.S. Application Data

(63) Continuation-in-part of application No. 09/246,907, filed on Feb. 9, 1999, now abandoned, which is a continuation-in-part of application No. 08/949,520, filed on Oct. 14, 1997, now abandoned.

(51) Int. Cl.$^7$ .................................................... G01N 33/00
(52) U.S. Cl. .................................. 436/88; 436/15; 435/4
(58) Field of Search .................................. 435/4; 436/15, 436/88

(56) References Cited

PUBLICATIONS

Rhoades et al. Medical Physiology, Little, Brown and Company New York p. 423, 1995.*

* cited by examiner

*Primary Examiner*—Patrick J. Nolan
(74) *Attorney, Agent, or Firm*—Jerome L. Jeffers

(57) ABSTRACT

Disclosed is an improved method for determining the concentration of a first analyte in a fluid test sample as a function of a second analyte also present in the sample whose concentration in the fluid sample is clinically related to that of the first analyte. The method involves determining the concentration of the first analyte, and, if this concentration is outside of its useful analytical range, dividing this concentration by the normal concentration of the second analyte. This method of ratioing the concentrations of the first and second analyte is advantageous because accuracy is increased with fewer false positive and false negative results being reported.

7 Claims, No Drawings

METHOD FOR IMPROVING THE ACCURACY OF THE SEMI-QUANTITATIVE DETERMINATION OF ANALYTE IN FLUID SAMPLES

This application is a Continuation-In-Part of application Ser. No. 9/246,907, filed Feb. 9, 1999, now abandoned, which in turn is a Continuation-In-Part of application Ser. No. 08/949,520 now abandoned filed on Oct. 14, 1997.

BACKGROUND OF THE INVENTION

Various analytical procedures and devices are commonly employed in assays to determine the presence and/or concentration of substances of clinical significance which may be present in biological fluids such as urine, whole blood, plasma, serum, sweat or saliva. Such substances are commonly referred to as analytes and can include specific binding partners, e.g. antibodies or antigens, drugs and hormones. One sort of test device is the so-called dipstick, containing enzymes or reagents which are interactive with the analyte and will interact with it in a manner which results in an indicator changing color which can be correlated with the presence or, in a semi-quantitative methods, the concentration of the analyte in the fluid sample. More recently there have been developed test strips which operate on the principle of immunochromatography in which labeled antibodies, specific for the analyte are applied to a strip of absorbant material through which the test fluid and labeled antibodies can flow by capillarity. By immobilizing analyte (or an analog thereof) in a particular portion of the strip, i.e. capture zone, and measuring the amount of labeled antibody which is captured through specific binding, the concentration of analyte in the test sample can be semi-quantitatively determined. This sort of assay, in which the label is an enzyme and there is placed a substrate for the enzyme in the capture zone to provide a colored response, is more fully described in U.S. Pat. No. 4,446,232. In U.S. Pat. No. 4,703,017 there is described a similar assay in which the label is a particulate material which, upon aggregation in the capture zone due to specific binding between the immobilized analyte and particle labeled antibody, provides a visible detectable response.

The clinical usefulness of analyses for various analytes can be enhanced by determining the concentration of a second analyte whose concentration in the biological fluid is clinically related to that of the first analyte. This is particularly true in urinalysis where the concentration of urine is very dependent on the degree of hydration, i.e. how hydrated the patient is as determined by fluid intake. In the case where a patient is dehydrated the urine is very concentrated and measurements tend to over predict an analyte's concentration which leads to false positive results. In the case of an overly hydrated patient, where the concentration of analytes is dilute, measurements tend to under predict the analyte's concentration leading to false negative results. Several analytes are known to measure urine concentration and are relatively unaffected by disease. The most notable example of the second analyte is creatinine, the end metabolite when creatine becomes creatine phosphate which is used as an energy source for muscle contraction and is, therefore, relatively constant for a given muscle mass. The creatinine produced is filtered by the kidney glomeruli and then excreted into the urine without reabsorption.

In order to increase the accuracy of urinary assays and minimize the problem of variable urine flow rates which result in urine dilution or concentration, analyte/creatinine ratios are used in urine protein assays to normalize the urine concentration. Common creatinine assays include the alkaline Jaffe and Benedict-Behre methods which are run at a high pH, typically in the range of from 11.5 to 12.5. More recently, there has been developed a creatinine assay in which the urine sample is contacted with cupric ions in the presence of citrate, a hydroperoxide and an oxidizable dye which provides a colored response in the presence of oxygen free radicals and a pseudoperoxide. Creatinine quantitation may also be accomplished immunologically as described in WO 96/34271. Those second analytes whose concentration in the sample of body fluid is clinically related to the concentration of the first analyte are not limited to creatinine in urine nor is urine the only body fluid which can be assayed by the method of the present invention. Thus, for example, the body fluid tested can be whole blood and the first analyte can be $HbA_{1c}$ with the second analyte being total hemoglobin since the apparent concentration of $HbA_{1c}$ can be adjusted to the whole blood's total hemoglobin concentration to factor out bias in the $HbA_{1c}$ assay. Inulin, administered intravenously, is, like creatinine, an indicator of renal flow. Typical of other first analytes which can be assayed in conjunction with creatinine as the second analyte are bacteria, red blood cells, leukocytes, various urinary proteins and glucose. The IgG concentration in urine can be corrected based on albumin as the second analyte.

In WO-96/34271 there is disclosed a device for determining a target (first) analyte and creatinine in a fluid test sample which device has an assay strip for the detection of creatinine and a second assay strip for the detection of the target analyte. The creatinine concentration may be determined colorimetrically or by the specific capture of labeled creatinine binding partners. The concentration of the target analyte is corrected based on the sample's concentration which correction can either be done manually or by means of a pre-programmed reflectance analyzer.

The prior art systems for determining the ratio of two analytes either involve a determination of the concentrations of both analytes followed by a determination of the ratio arithmetically or involve directly ratioing a response, such as color, due to the first analyte to the response due to the second analyte followed by converting the ratioed response to concentration values. This type of system is demonstrated in U.S. Pat. No. 5,385,847. The direct ratios of the colored responses is accomplished by first converting the colors into numerical values such as absorbance or reflectance for the first and second analytes. These numbers are divided and converted to a ratio result based on calibration. These systems for determining ratios are suitable in analytical procedures that have wide dynamic ranges due to small standard errors. The dynamic range is the useful range of analyte concentrations that the procedure is capable of measuring with accuracy. This imposes the requirement that the useful analytic range be determined is directly dependent on a method's accuracy. The bounds of the range are concentrations beyond which the method is not capable of measuring with accuracy. This is the concentration at which the procedure is not capable of determining an unknown concentration of analyte with reasonable certainty (typically >80%) as being different from the boundary limit. A method with an accuracy of a certain concentration of analyte such as 30 mg/L albumin is not useful for determining albumin at that concentration because the probability of the method being correct would equal the probability of the method being wrong.

The dynamic range for a ratio determined by two analytical procedures is always less than the range of either of the procedures by themselves due to a reduction in accuracy. The ratio determination is less accurate due to the addition of errors from both individual methods causing the error for the ratio determination to be increased. The ratio accuracy is defined by variance (or the square of the standard deviation) where:

$$Vx/y = Vx = X\ V1/y + VxX\mu^2 1/ + V1/yX\mu^2 x$$

in which V=variance; $\mu$=expected value; x/y=ration x=first analyte and y=second analyte.

With quantitative procedures, the dynamic range is wider than concentrations which are expected to be measured. The dynamic range of the procedures measuring the first and second analytes are so wide that the loss of range upon determining the ratio does not impact the usefulness of the ratio result. A method with a dynamic range of 5 to 500 mg albumin/g creatinine is capable of measuring an albumin to creatinine concentration in the medically useful range of 10 to 300 mg/gm as shown in U.S. Pat. No. 5,305,847. With semi-quantitative procedures, the dynamic ranges are narrowed since the methods have less accuracy than those which are quantitative. Additional reduction of accuracy and dynamic range due to the ratio calculation can have a negative impact on the usefulness of the ratio result. A dynamic range of 30 to 300 mg albumin/g creatinine is not capable of providing medically useful information at the boundary limits of the range, i.e. 30 or 300 mg/g.

SUMMARY OF THE INVENTION

The present invention involves an improvement to the analysis of a sample of body fluid for the concentration of a first analyte whose concentration in the body fluid is being sought and the concentration of a second analyte whose concentration in the fluid sample is clinically related to that of the first analyte wherein the ratio of the concentration of the first analyte to that of the second analyte is used to correct the concentration of the first analyte in the fluid sample. The improved method comprises the steps of:
  a) determining the observed concentrations of the first and second analytes using a semiquantitative analytical procedure for each;
  b) determining if the observed concentrations of the first and second analyte are inside or outside the threshold limits which are within the dynamic ranges of the semiquantitative analytical procedures;
  c) if the observed concentrations of the first and second analytes are outside the threshold limits, assigning the threshold limits closest to the observed values to the first and second analytes;
  d) if the observed value of the second analyte is the same as a threshold limit indicating an improper specimen discarding the assay result; and
  e) if the observed value of the first analyte is the same as a threshold limit, then assigning a ratio value by dividing the boundary limit of the first analyte by a constant representing the normal clinical concentration of the second analyte.

When the observed concentrations of the first and second analytes are inside the threshold limits then a ratio value is calculated by dividing the response of the analytical procedure for the first analyte by the response of the analytical procedure for the second analyte and assigning a output level to the ratio which corresponds to the concentration of the first analyte divided by that of the second analyte.

DESCRIPTION OF THE INVENTION

The first step in carrying out the present invention is to determine the observed concentration of the first and second analytes. This can be accomplished by applying the fluid test sample to a test strip either directly to the portion of the strip containing the reagents as in the case of an enzymatic reaction or, in the case of an immunochromatographic strip, to a sample application pad in fluid communication with the capture zone of the strip, so that the sample can flow to the capture zone by capillary action. In either case the color change caused by analyte in the test fluid interacting with the strip's reagents can be read manually by comparing the color with a standard color chart or, more accurately, with the aid of a reflectance meter.

Once the observed concentrations of the first and second analyte are determined, the next step is to ascertain if these concentrations are within the threshold limits of the useful analytical range of the methods used to determine these analytes. The term useful analytical range indicates the concentrations of analyte that the method is capable of measuring with accuracy. For example, the useful analytical range of the first analyte is the low boundary limit concentration to the upper boundary limit concentration which can be measured with accuracy based on the error of the estimate being substantially smaller, i.e. at least three times smaller, than the concentration of the analyte being estimated. If the determination of the first and second analyte are within these ranges, the ratio of first analyte to second analyte, i.e. [first analyte]/[second analyte] is calculated in the classical manner to provide an output level.

When the observed concentrations of the first and second analytes are outside the threshold limits, then the threshold limits closest to the observed values are assigned as the observed values. If the observed concentration of the second analyte is the same as the threshold value for this analyte, the ratio value is not calculated but instead the sample is flagged as an improper sample and the result is discarded. This is acceptable with semi-quantitative analytical methods which are used for screening to predict a quantitative value at a particular threshold as long as the threshold is within the dynamic range of the method. This is also acceptable when the method to measure the second analyte has a dynamic range that is larger than the range of concentration expected in all clinical samples.

If the observed concentration of the first analyte is the same as the threshold of the method then the concentration of the second analyte is not determined, but instead a constant which is the normal concentration of the second analyte is used to determine the ratio of first to second analyte by dividing the observed value of the first analyte by the constant to provide a ratio. The constant is determined by measuring the concentration of the second analyte for a population (typically greater than 1000 individuals) and calculating the average of all observed concentrations. Thus, in the case of creatinine, the constant is 0.66 g/L. The term normal concentration is intended to mean the expected physiological value obtained with typical healthy patients. This is in contrast to prior art ratioing methods in which the determined, rather than normal, concentration of the second analyte is used even in the cases where the concentration of the first analyte is determined to be outside of the useful analytical range. The method of the present invention provides greater precision in determining the concentration of the first analyte because values which are inaccurately determined are not allowed to have the additional error added to the result.

The present invention can be practiced using various body fluids such as blood, saliva and, in particular, urine. Included within the term are body secretions such as sweat, tears and prostatic fluid.

The method of practicing the present invention is further illustrated by the following examples.

Examples of Calculations of Albumin to Creatinine Ratio

In an analysis of urine in which albumin is the first analyte whose concentration is used to determine kidney status and creatinine is the second analyte whose concentration is determined to correct for renal flow, two analytical procedures are typically used to produce an albumin to creatinine ratio result.

The data presented in Table 2 compares the two prior art methods for calculating a ratio in the following examples 1 and 2 to the method in example 3 which is the subject of this invention. Table 2 shows the agreement of observed ratio results obtained with the semi-quantitative strip to the expected results obtained with the quantitative reference method. An agreement of 100w is ideal whereby the ratio results agree fully with the quantitative method results which are taken as accurate.

The following examples involve urine strip reagents which typically involve calorimetric assays whose color is read visually or instrumentally as reflectance or absorbance. The color produced is directly proportional to the analyte concentration. In the case of albumin, the more albumin reagent color formed, the more albumin is present in the urine specimen. In order to convert color to analyte concentration, a specific degree of color is assigned an output level. The output levels of an analyte are assigned a concentration range representing the typical error of the estimation. This is common practice for all urine reagent strips and is shown for albumin and creatinine reagents in the following Table 2. For example, a clinical specimen with a value of 30 mg/L albumin by a standard method could be 20 to 39 mg/L as determined by an albumin strip color but would still be assigned an albumin concentration of 30 mg/L. The smaller the error of the estimation, the more quantitative the method.

It is generally known that colors can only be measured within a certain absorbance range, typically less than 1.0 to greater than 0.1 absorbance or greater than 10% to less than 99% reflectance. For this reason, spectrometers and reflectance meters are typically programmed to provide a color outside this range the nearest color which the meter is able to measure. For example, a 7% reflectance is read as 10% reflectance and it is this value which is used in the determination.

TABLE 1

| Output Value | Albumin (mg/L) Expected Concentration Range | Output Value | Creatinine (mg/dL) Expected Concentration Range |
|---|---|---|---|
| 0 | 0–20 | 30 | 0–64.9 |
| 30 | 20–39.9 | 100 | 65.0–149.9 |
| 80 | 40–119.9 | 200 | 150.0–249.9 |
| 150 | 120–199.9 | 300 | 250.0–350.0 |

These limitations are typical of semiquantitative methods and cause predetermined dynamic ranges. The dynamic range for the albumin reagent used in all of the examples herein is 10 to 500 mg/L. The dynamic range of the creatinine reagent used is 10 to 350 mg/dL. The threshold limits for albumin and creatinine are defined by clinical studies relating disease to quantitative values. The medical decision (threshold limits) used were 20 to 200 mg/L albumin and 30 to 300 mg albumin/g of creatinine. Using the albumin and creatinine semi-quantitative methods and prior art methods, the dynamic range was estimated at 30 to 300 mg/g which is just at the threshold limit and, therefore, not accurate.

Example 1
Prior Art Method to Ratio Two Analytes

TABLE 2

| Ratio Method | Total Number of Correct Results | Remarks |
|---|---|---|
| Division | 70% | as in Ex. 1 |
| Color ratio method | 79% | as in Ex. 2 |
| Color ratio method with cut-off for out of bounds results | 95% | as in Ex. 3 |

From Table 2, it can be determined that greater assay accuracy can be obtained with the method of the present invention than with simple division or with a color ratio method that does not delete out of bounds results.

The most common prior art method to ratio two analytes is to use a look-up table (Table 3 below).

TABLE 3 mg Albumin/gram Creatinine Ratio Table: Assigned output

| | Albumin | | | |
|---|---|---|---|---|
| Creatinine | 0 mg/L | 30 mg/L | 80 mg/L | 150 mg/L |
| 30 mg/dL | <30 mg/g | 30–299 mg/g | 30–299 mg/g | 300 mg/g |
| 100 mg/dL | <30 mg/g | 30–299 mg/g | 30–299 mg/g | 30–299 mg/g |
| 200 mg/dL | <30 mg/g | <30 mg/g | 30–299 mg/g | 30–299 mg/g |
| 300 mg/dL | <30 mg/g | <30 mg/g | <30 mg/g | 30–299 mg/g |

Each combination of strip outputs is assigned an expected ratio output. The expected output ratio is bas ed on the division of the mean result of each strip as shown in Table 4.

TABLE 4 mg Albumin/gram Creatinine Ratio Table: Mean value of dividing each strip

| | Albumin | | | |
|---|---|---|---|---|
| Creatinine | 0 mg/L | 30 mg/L | 80 mg/L | 150 mg/L |
| 30 mg/dL | 0 | 100 | 267 | 500 |
| 100 mg/dL | 0 | 30 | 80 | 150 |
| 200 mg/dL | 0 | 15 | 40 | 75 |
| 300 mg/dL | 0 | 10 | 27 | 50 |

This method introduces error, since each mean output result represents an expected range and the extremes of the expected ranges do not always agree with the assigned output. For example, 30 mg/L albumin has a low extreme of 19.9 mg/L and 100 mg/dL creatinine has a high extreme of 150 mg/dL. The expected ratio output of these extremes is 13 mg/g which is not in the 30–299 mg/g assigned range. This erroneous assignment would be an incorrect ratio result even if the reagents agreed 100%. with the standard methods.

The error in this method is shown in the following truth table in which the strip results are compared to ratio values of 275 clinical specimens which were obtained with quantitative methods. The range of clinical specimen assigned a given albumin to creatinine strip output is much greater than the expected concentration range which makes this method inaccurate and ineffective. The total number of correct results for two levels of output, i.e. less than 30 mg/g and greater than 30 mg/g, is 70% (86 and 109 out of 225) with more than 35% of the >30 mg/g specimens being incorrectly assigned as can be determined by the 76 results out of 185 total results which are greater than 30 mg/g by the strip are less than 30 mg/g by the standard method.

Truth Table for Ratioing by Method of Example 1

| Standard methods | Albumin creatinine dipstick ratio | | |
|---|---|---|---|
| | <30 mg/g | >30 mg/g | total |
| <30 mg/g | 86 | 76 | 162 |
| >30 mg/g | 4 | 109 | 113 |
| total | 90 | 185 | 275 |

Example 2

Another common method to ratio two analytes known in the prior art is to convert the result of each individual reagent to concentrations of the analyte to be detected. This conversion is done by comparing a standard specimen having a known concentration to the unknown specimen and assigning to the unknown a concentration relative to the color differences of the two specimens. The analyte concentration can then be divided to produce a ratio of concentration. This approach is very common with colorimetric assay methods that have a high degree of accuracy. However, using this method with calorimetric assay methods having a lower degree of accuracy, for example urine dipstick methods, has a disadvantage since they have a smaller analytical range than solution methods which can make dilutions and timed addition of reagents to limit error increasing interferences. These quantitative methods have analytical ranges which extend beyond the concentrations which are expected to be encountered.

The results of this method of ratioing, as shown in the following Table 5, are only slightly better than the method discussed in Example 1. The total number of correct results for two levels of output is $$79\% \left(\frac{125 + 93}{275} = 0.79\right).$$

TABLE 5

Truth Table for Ratioing by Method of Example 2

| Standard methods | Albumin creatinine dipstick ratio | | |
|---|---|---|---|
| | <30 mg/g | ≧30 mg/g | total |
| <30 mg/g | 125 | 37 | 162 |
| ≧30 mg/g | 20 | 93 | 113 |
| total | 145 | 130 | 275 |

Example 3

The ratioing method of the present invention is used in example 3. The concentration of the albumin and creatinine were first determined as described as the common practice for the threshold limits described previously, i.e. the albumin reagent has a dynamic range of 10 to 500 mg/L and the creatine reagent has a dynamic range of 10 to 350 mg/L.

If the observed concentration of creatinine is outside the threshold range of the creatinine reagent, i.e. 25 to 250 mg/dL then a ratio value is not calculated and instead is flagged as an improper sample and the result is discarded. Threshold ranges for creatinine and other analytes are determined by measuring the concentrations of the analytes from a large population of individuals (typically greater than 1000) using quantitative methods. Threshold ranges for creatinine and other analytes are determined by measuring the concentration of the analytes for individuals in large population using quantitative methods. The observed range of values are calculated for the condition of the individuals (i.e. those in normal health and those with disease). Threshold values are the range of values that encompass most of the individuals (>95% with a given condition. The creatinine reagent has a dynamic range, which must be wider than the threshold limits, of 10 to 350 mg/dL. This dynamic range is wider than the expected range of concentration, i.e. threshold limit, of >25 to <250 mg/dL that is observed in clinical specimens. A creatinine result of 10 mg/dL can be accurately measured and would indicate an improper or atypical specimen because its creatinine concentration was below the threshold limit for creatinine in normal individuals and the result would be discarded.

A sample with a creatinine concentration below the threshold of 25 mg/dL is extremely dilute and is at high risk of producing a false negative ratio result. As a screening result which tries to avoid all false negatives, it is more practical to obtain another specimen from the patient than to use the potentially misleading results. It is possible to use only the <25 mg/dL threshold since a specimen with a >250 mg/dL creatinine concentration is an overly concentrated urine specimen and at risk of producing a false positive ratio result. Since all positives are to be confirmed, there is no chance of a misleading result being used.

Next, the color of the reagent which is sensitive to the first analyte, albumin in this case, is converted to the concentration of the first analyte, i.e. a specific degree of color is assigned an output value. The output level is examined and if the level is outside the threshold of 20 to 200 mg/L, it is used to assign a ratio by using the normal value of the second analyte. For example, an albumin reagent producing a result of less than 20 mg/L or greater than 200 mg/L of urine is assigned an output ratio without reference to the creatinine reagent result and instead using a constant representing the normal creatine value. In the case of creatinine, this value is the value of 0.66 g/L since the body typically excretes 1.33 g of creatinine and 2.0 L per day. Albumin at a concentration of less than 20 mg/L is assigned an albumin value of 20 mg/L which is the closest threshold limit and a ratio of <30 mg/gm which is 20 mg/L albumin divided by the normal creatine value of 0.66 g/L. Albumin at greater than 200 mg/L is assigned an albumin value of 200 mg/L (the closest threshold limit) and a ratio of >300 mg/gm which is 200 mg/L albumin divided by the normal creatinine value of 0.66 g/L. This assignment assumes average creatinine excretion of 0.66 g/L.

If the output of the first analyte is inside the threshold range, the color formed by the reagent which is sensitive to the first analyte is divided by the color formed by the reagent which is sensitive to the second analyte. The ratio of colors is then converted to a ratio concentration as in Table 6.

TABLE 6

| Output Value* | Color Ratio |
|---|---|
| <30 | <1.5 |
| 30–300 | 1.5 to 3 |
| >300 | >3 |

*mg albumin/g creatinine

For example, an albumin reagent producing a result of 80 mg/L is assigned an output ratio based on the color ratio of the albumin and creatine reagents, in which case a color ratio of 1.7 would be assigned an output ratio of 30-300 mg/g.

The following Table 7 shows that this method has a greater agreement than either of the previously described methods. The greater agreement is due to excluding the greater error often observed with a reagent at the ends of its output range, i.e. past the lowest or highest output levels. Results outside the analytical range have large errors and are inaccurate. Either or both the lowest and highest output levels can be excluded for any reagent being ratioed. In the Table 7, the total number of correct results for two levels of output, i.e. less than 30 mg/g or greater than 30 mg/g is 95%. This can be determined by the number of specimens correctly determined (149+112) divided by 275 which is the total number of specimens.

TABLE 7

Truth Table for Ratioing by Method of Example 3

| Standard methods | Albumin creatinine dipstick ratio | | |
|---|---|---|---|
| | <30 mg/g | ≧30 mg/g | Total |
| <30 mg/g | 149 | 13 | 162 |
| ≧30 mg/g | 1 | 112 | 113 |
| total | 150 | 125 | 275 |

What is claimed is:

1. An improvement to the analysis of a sample of urine for the concentration of albumin using the concentration of creatinine to correct the concentration of albumin which improvement comprises:
   a) determining the observed concentrations of albumin and creatinine using a semi-quantitative analytical procedure for each;
   b) determining if the observed concentration of albumin and creatinine are inside or outside threshold limits which are within the dynamic ranges of the semiquantitative analytical procedures;
   c) if the observed concentrations of albumin and creatinine are outside the threshold limits, then assigning the threshold limits closest to the observed value as the observed concentrations;
   d) if the observed value of the creatinine is the same as a threshold limit, then indicating an improper specimen which is discarded; or
   e) if the value of the albumin is the same as a threshold limit, then assigning a ratio value by dividing the threshold limit of the albumin by a value representing the normal clinical concentration of the creatinine.

2. The analysis of claim 1 wherein the threshold limits for the albumin and creatinine are determined by measuring the concentration of these analytes in the urine of a large number of individuals using quantitative methods.

3. The analysis of claim 1 wherein the dynamic range for the reagent to measure creatinine is 10 to 350 mg/dL and the threshold limits for creatinine are between 25 and 250 mg/dL.

4. An assay for albumin in a urine sample which comprises the steps of:
   a) determining the observed concentration of albumin in the urine sample and the observed concentration of creatinine in the urine sample by a semi-quantitative method, which has a dynamic range for creatinine greater than 25 to 250 mg/dL;
   b) determining if the observed concentration for creatinine is inside or outside the dynamic range of 25 to 250 mg/dL for creatinine;
   c) if the observed concentration for creatinine is less than 25 or greater than 250 mg/dL then treating the results as erroneous and discarding them; or
   d) if the observed concentration for albumin is outside of its closest threshold limit, assigning a value for the threshold limit for albumin by 0.66 g/L to obtain the corrected concentration of the albumin.

5. The assay of claim 4 wherein the first analyte is albumin whose assigned range of threshold limits is 20 mg/L to 200 mg/L, the observed concentration for albumin is greater than 200 mg/L and the 200 mg/L upper threshold is divided by 0.66 g/L to give an albumin concentration of greater than 300 mg/gm.

6. The assay of claim 4 wherein the threshold limits for a particular analyte area determined by measuring the concentration of the analyte for individuals in a large population using a quantitative method.

7. An assay for albumin in a urine sample which comprises the steps of:
   a) determining the observed concentration of albumin in the urine sample and the observed concentration of creatinine in the urine sample by a semi-quantitative method which has a dynamic range for creatinine of greater than 25 to 250 mg/L;
   b) determining if the observed concentration for creatinine is inside or outside the dynamic range of 25 to 250 mg/dL for creatinine;
   c) if the observed concentration for creatinine is less than 25 or greater than 250 mg/dL then treating the results as erroneous and discarding them; or
   d) if the observed concentration for albumin is greater than 200 mg/L then dividing the observed concentration by 0.66 g/L to give an albumin concentration of greater than 300 mg/gm.

* * * * *